US 6,466,808 B1

(12) United States Patent
Chin et al.

(10) Patent No.: US 6,466,808 B1
(45) Date of Patent: Oct. 15, 2002

(54) SINGLE DEVICE FOR BOTH HEATING AND TEMPERATURE MEASUREMENT IN AN OXIMETER SENSOR

(75) Inventors: Rodney Chin, Oakland; Steven Hobbs, Pleasanton, both of CA (US)

(73) Assignee: Mallinckrodt Inc., Hazelwood, MO (US)

( * ) Notice: Subject to any disclaimer, the term of this patent is extended or adjusted under 35 U.S.C. 154(b) by 0 days.

(21) Appl. No.: 09/447,449

(22) Filed: Nov. 22, 1999

(51) Int. Cl.[7] .................................................. A61B 5/00
(52) U.S. Cl. ...................... 600/323; 600/334; 600/322
(58) Field of Search ................................ 600/309–310, 600/322, 326–334; 356/39–41

(56) References Cited

U.S. PATENT DOCUMENTS

| 4,429,700 | A | * | 2/1984 | Thees et al. ................ 600/494 |
| 4,739,771 | A | * | 4/1988 | Manwaring ................. 600/504 |
| 4,825,879 | A | | 5/1989 | Tan et al. |
| 4,859,078 | A | * | 8/1989 | Bowman et al. .............. 374/44 |
| 4,872,458 | A | * | 10/1989 | Kanehira et al. ............ 606/31 |
| 4,890,619 | A | | 1/1990 | Hatschek |
| 4,926,867 | A | | 5/1990 | Kanda et al. |
| 5,007,423 | A | * | 4/1991 | Branstetter et al. ......... 600/334 |
| 5,218,961 | A | * | 6/1993 | Lekholm ..................... 607/22 |
| 5,299,570 | A | | 4/1994 | Hatschek |
| 5,392,777 | A | | 2/1995 | Swedlow et al. |
| 5,425,868 | A | * | 6/1995 | Pedersen .................... 204/408 |
| 5,638,816 | A | | 6/1997 | Kiani-Azarbayjany et al. |
| 5,720,293 | A | * | 2/1998 | Quinn et al. ................ 600/505 |
| 5,832,921 | A | * | 11/1998 | Lennert et al. ............. 600/309 |
| 5,860,919 | A | | 1/1999 | Kiani-Azarbayjany et al. |
| 6,285,896 | B1 | * | 9/2001 | Tobler et al. ............... 600/338 |

* cited by examiner

Primary Examiner—Eric F. Winakur
Assistant Examiner—Matthew Kremer
(74) Attorney, Agent, or Firm—Townsend & Townsend & Crew LLP

(57) ABSTRACT

A method and apparatus for both heating a patient's skin and for measuring the temperature using the same device, such as a thermistor. Thus, the thermistor generates controlled heat, and is not just used for sensing the temperature. In an oximetry sensor, the thermistor is located in the vicinity of the light emitter and photodetector to warm the optically-probed tissue region. As heat is dissipated, temperature changes are sensed as resistance changes according to Ohm's law. Active thermal regulation by varying the amount of thermistor current and power can safeguard against burning the tissue while maximizing perfusion.

27 Claims, 2 Drawing Sheets

SINGLE DEVICE FOR BOTH HEATING AND TEMPERATURE MEASUREMENT IN AN OXIMETER SENSOR

BACKGROUND OF THE INVENTION

The present invention relates to oximeter sensors, and in particular oximeter sensors with a heating element to improve perfusion.

Pulse oximetry is typically used to measure various blood characteristics including, but not limited to, the blood-oxygen saturation of hemoglobin in arterial blood, and the rate of blood pulsations corresponding to a heart rate of a patient. Measurement of these characteristics has been accomplished by use of a non-invasive sensor which passes light through a portion of the patient's tissue where blood perfuses the tissue, and photoelectrically senses the absorption of light in such tissue. The amount of light absorbed is then used to calculate the amount of blood constituent being measured.

The light passed through the tissue is selected to be of one or more wavelengths that are absorbed by the blood in an amount representative of the amount of the blood constituent present in the blood. The amount of transmitted or reflected light passed through the tissue will vary in accordance with the changing amount of blood constituent in the tissue and the related light absorption. For measuring blood oxygen level, such sensors have been provided with light sources and photodetectors that are adapted to operate at two different wavelengths, in accordance with known techniques for measuring blood oxygen saturation.

Heaters have been used in sensors to improve the perfusion, or amount of blood, adjacent the sensor. This will thus improve the measurement since the light will encounter a larger volume of blood, giving a better signal-to-noise ratio for the oximeter reading.

U.S. Pat. No. 4,926,867 shows a piece of metal used as a heater in an oximeter sensor. A separate thermistor is used to measure the amount of heat so that the heater can be controlled to avoid burning the patient.

U.S. Pat. Nos. 5,299,570 and 4,890,619 both show ultrasonic elements being used for perfusion enhancement.

Because the normal human body core temperature is approximately 37° C., and burning of tissue could take place for temperatures above approximately 42–43° C., a tight range of control of the heating element is required. Another challenge is the heat gradient and delay time between the heating element and the temperature measuring element.

SUMMARY OF THE INVENTION

The present invention provides a method and apparatus for both heating a patient's skin and for measuring the temperature using the same device, such as a thermistor. Thus, the thermistor generates controlled heat, and is not just used for sensing the temperature. In an oximetry sensor, the thermistor is located in the vicinity of the light emitter and photodetector to warm the optically-probed tissue region. As heat is dissipated, temperature changes are sensed as resistance changes according to Ohm's law. Active thermal regulation by varying the amount of thermistor current and power can safeguard against burning the tissue while maximizing perfusion.

It has been shown recently that general warming of the tissue region increases the amount of blood perfused in the tissue. This increased perfusion substantially strengthens the pulse oximetry signal. Benefits include quick signal acquisition, increased accuracy, and greater tolerance to motion artifact.

In one embodiment, the thermistor is a positive temperature coefficient (PTC) thermistor rather than the more common, negative temperature coefficient (NTC) thermistor. The PTC provides a highly desirable safety feature as poor connections yield a perceived, higher-than-normal resistance indication. As a result, the actual thermistor temperature is regulated at a lower-than-expected temperature, avoiding the chance of burns.

Another advantage of the same thermistor being used for both generating heat and temperature measurement is that there is no thermal gradient between the heating element and the sensing element as in the prior art. This allows for a faster response time, which is critical for maintaining a tight temperature range.

The thermistor's resistance can be conventionally determined either by a two-wire or a four-wire method. The four-wire method is typically used when the connections used in the two-wire method would have resistances that could significantly affect the measurement. In the four-wire method, one pair of wires is used to inject a known current through the thermistor, while the other pair is used to sense the voltage across the thermistor. This enables a highly accurate determination of the thermistor's temperature.

In an alternate embodiment, a simple bridge circuit with a setpoint resistor may be used to automatically bias the thermistor at a particular resistance/temperature. Once the thermistor's desired operating resistance is known from the factory, the appropriate value of the setpoint resistor can be employed in the circuit. This simple circuit could be integrated into the sensor itself or in the remote monitor.

For a further understanding of the nature and advantages of the invention, reference should be made to the following description taken in conjunction with the accompanying drawings.

DESCRIPTION OF THE SPECIFIC EMBODIMENTS

Figure 1:
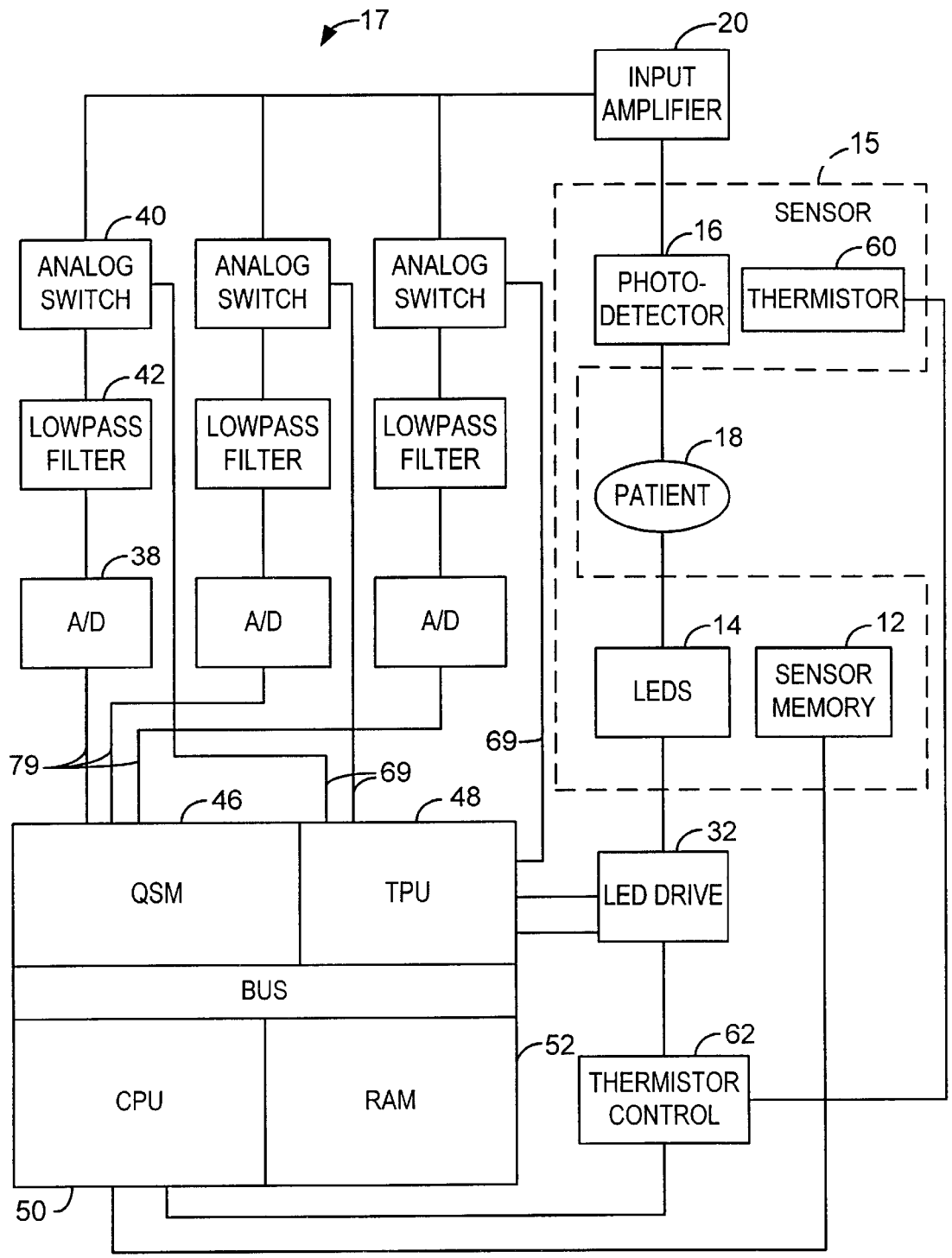
FIG. 1 is a diagram of a pulse oximetry system including the present invention.

FIG. 1 is a block diagram of one preferred embodiment of the invention. FIG. 1 shows a pulse oximeter 17 (or sensor reader) which is connected to a non-invasive sensor 15 attached to patient tissue 18. Light from sensor LEDs 14 passes into the patient tissue 18, and after being transmitted through or reflected from tissue 18, the light is received by photosensor 16. Either two or three LEDs or other light sources can be used depending upon the embodiment of the present invention. Photosensor 16 converts the received energy into an electrical signal, which is then fed to input amplifier 20.

Light sources other than LEDs can be used. For example, lasers could be used, or a white light source could be used with appropriate wavelength filters either at the transmitting or receiving ends. The light could be delivered to the patient site with fiber optics, with the light source in the sensor or remotely located.

Time Processing Unit (TPU) 48 sends control signals 68 to the LED drive 32, to alternately activate the LEDs, typically in alteration. Again, depending on the embodiment, the drive may control two or any additional desired number of LEDs.

Figure 3:
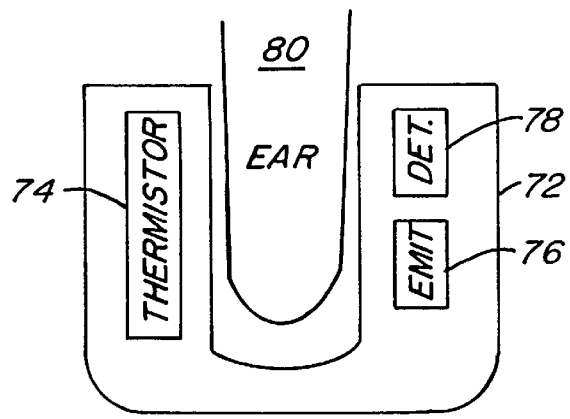
FIG. 3 is a diagram of an embodiment using a large area thermistor and a reflective type oximeter sensor.

The signal received from input amplifier 20 is passed through three different channels as shown in the embodiment of FIG. 3 for three different wavelengths. Alternately, two channels for two wavelengths could be used, or N channels for N wavelengths. Each channel includes an analog switch 40, a low pass filter 42, and an analog to digital (A/D) converter 38. Control lines 69 from TPU 48 select the appropriate channel at the time the corresponding LED 14 is being driven, in synchronization. A queued serial module (QSM) 46 receives the digital data from each of the channels via data lines 79. CPU 50 transfers the data from QSM 46 into RAM 52 as QSM 46 periodically fills up. In one embodiment, QSM 46, TPU 48, CPU 50 and RAM 52 are part of one integrated circuit, such as a microcontroller.

A thermistor 60 is shown mounted in sensor 15. Thermistor 60 could be mounted adjacent the photodetector or the LEDs, or nearby. A thermistor control circuit 62 provides the power and current to the thermistor to deliver the desired heat, while measuring the resulting resistance, and thus the temperature. The thermistor can either be a positive temperature coefficient (PTC) or a negative temperature coefficient (NTC) thermistor.

The thermistor is used in a dual capacity to dissipate thermal heat energy and self-monitor its temperature for the safe operation in a "warmed" oximeter sensor.

A positive temperature coefficient (PTC) thermistor is more desirable than a negative temperature coefficient (NTC) thermistor for oximetry/medical applications. For a given voltage source applied to the thermistor, the power dissipation decreases with increasing temperature due to the increased resistance at higher temperatures. Additionally, if there exists connection resistances within the sensor cable and/or connections, the increased series resistance would be perceived by the oximeter as a falsely higher temperature. This is desirable as the oximeter would regulate the sensor at a lower (safe) temperature and avoid the possibility for patient burns. Since PTC thermistors generally have thermal coefficients that are smaller than for NTC, special PTC thermistors may be used. The nonlinear behavior of the switching or nonlinear PTC thermistors is desirable. These are available from Advanced Thermal products, St. Mary's, PA and other sources. The material is processed so the switching temperature is between 40–50° C., generally.

In one embodiment, it is desirable to have a PTC transistor with a phase transition, where the resistance suddenly increases, in the region between 40–50° C. This can be controlled in a number of different ways, such as by appropriate doping of the thermistor material.

In practice, the PTC thermistor is regulated at 39–41° C. This is just slightly above normal (37° C.) core body temperature but below the burn threshold of 42–43° C. It has been shown recently that general warming of the tissue region probed by the oximetry sensor increases localized perfusion and increases the strength of the pulsatile oximetry signal. The benefit of this includes an increase in the acquisition and accuracy of the oximetry measurement and an increase in the tolerance to motion artifact.

An advantage of the same thermistor being used for both generating heat and for measuring it is that there is no thermal gradient between the heating element and the sensing element as in the prior art. This allows for a faster response time, which is critical in maintaining a temperature within a tight range, as required.

Figure 2:
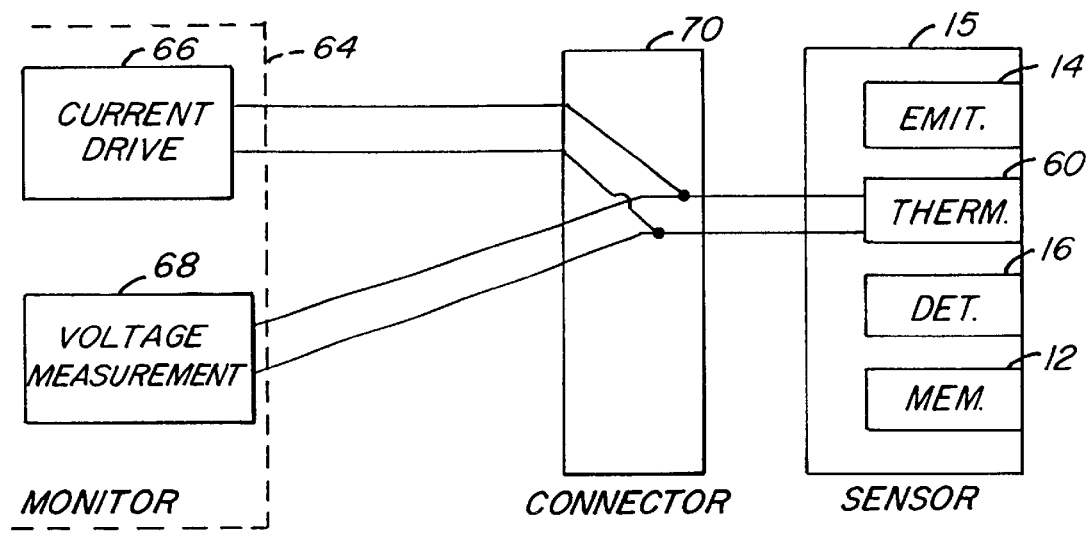
FIG. 2 is a diagram illustrating four-wire measurement in one embodiment of the invention.

FIG. 2 illustrates a four-wire measurement system for a thermistor of the present invention. FIG. 2 shows a monitor 64 with a current drive circuit 66 and a voltage measurement circuit 68. Each are separately connected by two wires to a connector 70 close to sensor 15. From connector 70, the four wires are converted into two wires for connecting to the actual sensor. Alternately, the four wires can extend all the way to thermistor 60.

Current drive circuit 66 is programmable to provide the appropriate amount of current to achieve the desired power dissipation and temperature through thermistor 60. Voltage measurement circuit 68 simultaneously measures the resulting voltage, which will allow the determination of the resistance from the known drive current. By using four wires to a position close to the sensor, the resistance effects of the wiring and any connections are also taken into account.

The other connections in FIG. 2 are not shown in order not to obscure the connections of the thermistor. Memory chip 12 in one embodiment is used to store thermal coefficients of the thermistor or other thermal parameters of the sensor. These parameters can then be read by the oximeter monitor 64 and used by its CPU 50 to determine an appropriate drive current for the thermistor. The temperature control is done in part by the hardware and in part by software in the CPU. The amount of power dissipated in the thermistor is controlled by the resistance measurement, which corresponds to a temperature measurement.

The sensor could be any type of sensor, such as a durable sensor or a disposable sensor. It could attach to any body part, such as the earlobe, finger, etc. The sensor could be a reflectance or a transmittance sensor.

Since commercially available thermistors often vary significantly in their actual resistance value, the thermistors can either be trimmed at the factory, or a precision resistor could be placed in series or in parallel to adjust the resistance to the desired value.

In one embodiment, shown in FIG. 3, the sensor 72 uses a single thermistor element 74 with a reflectance geometry. The thermistor is opposite to the reflectance sensor emitter 76 and detector 78. this allows a large warming surface to contact the tissue 80 for the ear sensor.

The thermistor need not directly contact the skin because the thermal loading could be asymmetrically strong to cause a lengthwise thermal gradient and an error in the temperature measurement. The thermistor is in close contact for maximum heat transfer but is somewhat embedded inside the sensor housing. A thin layer between the thermistor and contact surface may act as a buffer to allow a uniform, heat-spreading action.

Figure 4:
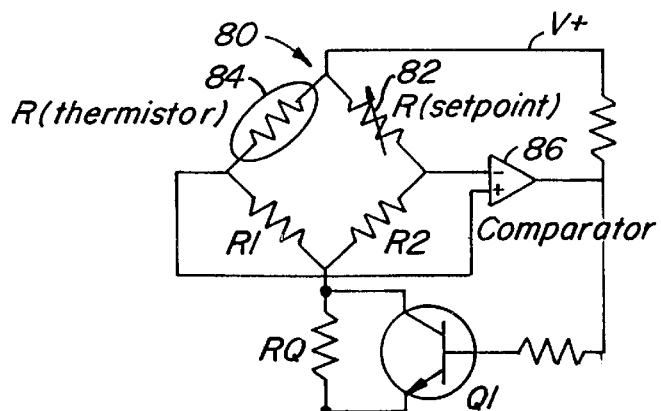
FIG. 4 is a circuit diagram of an embodiment of a bridge circuit for regulating the thermistor temperature.

FIG. 4 is a circuit diagram of an alternate embodiment which allows a thermistor to be set to a desired temperature without intervention by a microprocessor.

A floating resistive bridge circuit 80 can be biased at high or low current. Alternately, this current bias can be made continuously adjustable. The nulling of the bridge signifies when the setpoint temperature has been met. A setpoint resistor 82 is adjusted for the proper setpoint temperature (resistance) of the thermistor 84. When the thermistor's resistance (temperature) is too high, a comparator circuit 86 is switched to cause the bridge to be biased in the low current mode to minimize the current through the thermistor (by turning off transistor Q1, forcing the current through resistor RQ). Conversely, then the thermistor's resistance (temperature) is too low, the comparator circuit is switched to cause the bridge to be biased in the high current mode supplying more current and thus more power to the thermistor (turning on transistor Q1, bypassing resistor RQ). There must be some voltage (current) supplied to the bridge to allow for sensing of the thermistor's resistance for the null measurement of the bridge circuit.

Obviously, a more elaborate thermal regulation circuit could be built. However, it has been found that this circuit works very well with no significant temperature overshoot/undershoot. This is due to the intrinsic self-measurement nature of the system with no thermal delay time between the warming element and the temperature sensor. Typical maximum power dissipation for effective application of a warmed earlobe sensor is less than 0.5 watts per side. With proper heat spreading, the thermistor is efficient at delivering the thermal energy without incurring a large thermal gradient from the thermistor to the tissue. This would give the best tissue temperature and the best performance.

Because of the simplicity of the circuit with few components, it is possible to integrate the whole circuit in the oximetry sensor assembly. The circuit consists of only a few components as shown. The benefit of this would be the requirement of only a single power supply connection and utilizing an existing ground connection. An adapter cable could be used with older instruments to supply the additional supply lead.

As will be understood by those of skill in the art, the present invention may be embodied in other specific forms without departing from the essential characteristics thereof. For example, the thermistor could be placed at any location on the sensor, and some or all of the monitoring or drive circuit could be located on the sensor, on an adapter or connector, or in a remote monitor. Accordingly, the foregoing description is intended to be illustrative, but not limiting, of the scope of the invention which is set forth in the following claims.

What is claimed is:

1. A method for operating an oximeter sensor, comprising:
    activating a light source to provide light to a patient,
    detecting light from said patient;
    providing power to a device to heat said patient with said device;
    determining temperature from said same device; and
    modifying the amount of power provided to said device in accordance with said temperature, wherein said providing power and said determining temperature are done using same said device and wherein said device is an inherently self-regulating heating device and wherein said device is not in direct contact with said patient.

2. The method of claim 1 wherein said device is a thermistor, and a resistance of said thermistor is measured to determine said temperature.

3. The method of claim 2 wherein said thermistor is a positive temperature coefficient thermistor.

4. The method of claim 3 wherein said thermistor is a switching thermistor.

5. The method of claim 4 wherein said thermistor switches at a temperature between 30 and 55 degrees centigrade.

6. The method of claim 2 wherein said resistance of said thermistor is measured using a four wire measurement.

7. The method of claim 1 further comprising:
    storing at least one calibration value corresponding to a characteristic of said device;
    reading said calibration value; and
    modifying the operating temperatures of said device in accordance with said calibration value.

8. The method of claim 2 wherein said power provided to said thermistor is provided by supplying a current to said thermistor.

9. A method for operating an oximeter sensor, comprising:
    activating a light to provide light to a patient;
    detecting light from said patient;
    providing a thermistor in said sensor, said thermistor being a switching thermistor that switches between 30 and 55 degrees centigrade, said thermistor having a positive temperature coefficient;
    providing power to said thermistor to generate an amount of heat to heat said patient with said thermistor;
    measuring the resistance of said thermistor using a four wire measurement;
    determining temperature from said measurement of the resistance of said thermistor; and
    modifying the amount of current provided to said thermistor in accordance with said amount of heat, wherein said thermistor is not in direct contact with said patient.

10. The method of claim 9 further comprising:
    storing at least one calibration value corresponding to a characteristic of said thermistor;
    reading said calibration value; and
    modifying the operating temperature of said thermistor in accordance with said calibration value.

11. An oximeter sensor comprising:
    a light source mounted to provide light to a patient;
    a light collector mounted to collect light from said patient;
    a device, mounted proximate at least one of said light some and said light collector, said device being controllable to both heat said patient and also measure the temperature, wherein said device is a positive temperature coefficient thermistor, and wherein said device is not in direct contact with said patient when performing a measurement.

12. The sensor of claim 11 wherein said thermistor is a switching thermistor.

13. The sensor of claim 12 wherein said thermistor switches at a temperature between 30 and 55 degrees centigrade.

14. The sensor of claim 11 further comprising four wires connected to said thermistor for use in a four wire measurement technique.

15. The sensor of claim 11 further comprising a memory storing at least one calibration value corresponding to a characteristic of said device.

16. An oximeter sensor comprising:
    a light source mounted to provide light to a patient;
    a light collector mounted to collect light from said patient;
    a thermistor, mounted proximate at least one of said light source and said light collector, said thermistor being controllable to both heat said patient and also measure the temperature, wherein said thermistor is not in direct contact with said patient when performing a measurement;
    said thermistor being a positive temperature coefficient thermistor;
    said thermistor being a switching thermistor that switches at a temperature between 30 and 55 degrees centigrade; and
    four wires connected to said thermistor for use in a four wire measurement technique.

17. An oximeter system comprising:
a sensor including
a light source mounted to provide light to a patient;
a light collector mounted to collect light from said patient;
a device, mounted proximate at least one of said light source and said light collector, wherein said device is an inherently self-regulating heating device;
a monitor including
a control circuit connected to said device to control said device to both heat said patient and also measure the temperature by measuring the resistance of said device wherein said device is not in direct contact with said patient when performing a measurement.

18. The oximeter system of claim 17 wherein said device is a thermistor.

19. The oximeter system of claim 18 further comprising four wires connecting said control circuit to said thermistor.

20. The oximeter system of claim 18 wherein said thermistor is a positive temperature coefficient thermistor.

21. The oximeter system of claim 18 wherein said control circuit
comprises a bridge circuit having a setpoint resistor with a value selected to set an operating resistance of said thermistor.

22. The oximeter system of claim 18 wherein said control circuit controls the current bias to said thermistor to control the power delivered to said thermistor.

23. The oximeter system of claim 18 wherein said control circuit controls the power delivered to said thermistor using pulse width modulation of the current.

24. The oximeter system of claim 23 wherein the pulse width modulation current is switched while said light source is off.

25. The oximeter system of claim 23 wherein the pulse width modulation current is switched while said light collector signal is not measured.

26. An oximeter system comprising:
a sensor including:
a light source mounted to provide light to a patient;
a light collector mounted to collect light from said patient and to provide a signal;
a thermistor, mounted proximate to at least one of said light source and said light collector, wherein said thermistor is a positive temperature coefficient thermistor, and wherein said thermistor is not in direct contact with said patient when performing a measurement, and wherein said thermistor being controllable to both heat said patient and also measure the temperature;
a monitor including:
a control circuit connected to said thermistor to control the setpoint temperature of said thermistor; and
a processor unit to determine a parameter of signal quality derived from said patient.

27. The oximeter system of claim 26 wherein said control circuit adjusts the setpoint temperature of said thermistor depending upon the state of said signal.

* * * * *